United States Patent [19]

Hulshof

[11] 4,336,401
[45] Jun. 22, 1982

[54] PROCESS FOR THE PREPARATION OF DAMASCENONE

[75] Inventor: Lumbertus A. Hulshof, Hoevelaken, Netherlands

[73] Assignee: Hercules Incorporated, Wilmington, Del.

[21] Appl. No.: 169,681

[22] Filed: Jul. 17, 1980

[51] Int. Cl.³ .................. C07C 69/76; C07C 67/02
[52] U.S. Cl. .................... 560/106; 560/259; 560/260; 568/378
[58] Field of Search .............. 560/106, 259, 260; 568/378

[56] References Cited

U.S. PATENT DOCUMENTS 3,946,078 3/1976 Rautenstrauch .................. 568/378

OTHER PUBLICATIONS

Helv. Chim. Acta 56: 1503 (1973) 1503–13.

Primary Examiner—Paul J. Killos
Attorney, Agent, or Firm—William S. Alexander

[57] ABSTRACT

A novel method of preparing 1-crotonoyl-2,6,6-trimethylcyclohexa-1,3-diene comprises treating an ester of the formula

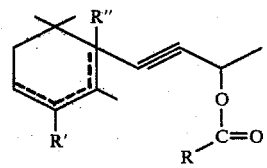

with a proton acid under essentially anhydrous conditions.

10 Claims, No Drawings

PROCESS FOR THE PREPARATION OF DAMASCENONE

The present invention relates to a novel process for preparing 1-crotonoyl-2,6,6-trimethylcyclohexa-1,3-diene having the formula:

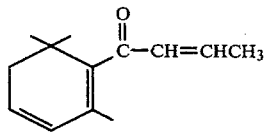

The invention further relates to novel starting materials used in the said process.

The compound of formula I, 1-crotonoyl-2,6,6-trimethylcyclohexa-1,3-diene, is a highly odoriferous compound found in nature as a trace component in several fruits such as, e.g., raspberry, apple and grapes, and several plant species such as deer tongue, tobacco, peppermint and Bulgarian rose, and in beer, wines, and rum. Its organoleptic and olfactory properties make it useful as a component in aromas and perfume compositions and as an aroma-additive to foodstuffs, beverages, pharmaceuticals and tobacco products. It is also used in the preparation of synthetic essential oils such as mock-orange and rose oil.

Because of the growing industrial importance of the compound and its limited availability from natural sources, much attention has been directed to the synthesis of 1-crotonoyl-2,6,6-trimethylcyclohexa-1,3-diene and to the structurally related compounds which are also of industrial interest. The interest in the compound is demonstrated by the numerous methods of preparation which have been reported, e.g., German patent application Nos. 1,807,568, 2,022,216, 2,065,322, 2,605,323, 2,065,324, 2,240,311, 2,242,751, 2,244,680 and 2,305,140; Dutch patent application No. 75.10914; U.S. Pat. No. 3,928,456; Swiss Pat. Nos. 563,326 and 548,967; French Pat. No. 2,174,306; Japanese patent application Nos. 74.75556 (Chem. Abstr. 82, 124888 (1975)) and 75.69048 (Chem. Abstr. 84, 30532 (1976)), Helv. Chim. Acta 53, 541 (1970), ibid.54, 1767, 1899 (1971), ibid.56, 310, 1503, 1514 (1973), J.C.S. Chem. Commun. 1973, 161 and J.C.S. Perkin Trans. I, 1975, 1727.

Most of the synthetic methods described in these references are laboratory methods which are not readily adaptable to profitable commercial use.

It is the object of the present invention to provide a method of preparing crotonoyl-2,6,6-trimethylcyclohexa-1,3-diene in a technically simple and commercially feasible manner which suppresses the yield of undesirable by-products.

The process of the invention comprises treating an ester of the formula

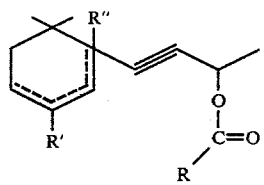

where R is a 1 to 6 carbon alkyl group, a phenyl radical or an alkylphenyl radical, the dotted lines represent a sole double bond in the 1-or 2-position or conjugated double bonds in the 1,3-position, and when the double bond is in the 1-position only, R' is hydroxyl or

and R" is absent, when the double bond is in the 2-position, R" is hydroxyl and R' is absent, and when conjugated double bonds are present, R' is hydrogen and R" is absent, with an essentially anhydrous mineral acid or organic proton acid in an organic solvent capable of forming an azeotrope with water.

The esters according to formula II are novel compounds represented by four species having the general formulae III to VI

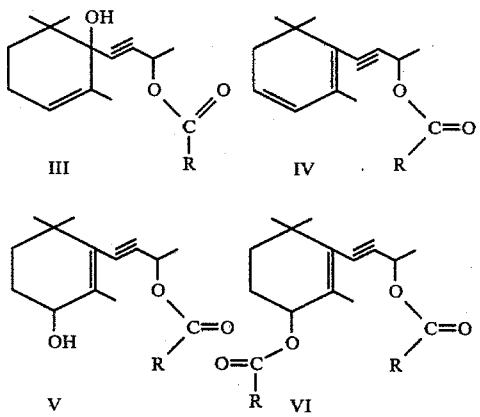

The esters of formula III are prepared by direct acylation of the diol 2,6,6-trimethyl-1-hydroxyl-1-(3-hydroxy-but-1-ynyl)cyclohex-2-ene. This diol is a known compound which can be prepared by reacting 2,6,6-trimethyl cyclohex-2-ene-1-one with 3-hydroxy-but-1-yne in the presence of a lithium alkyl, a Grignard reagent, or metallic lithium and ammonia. See, e.g., Japanese patent application No. 74/75556 or British Pat. No. 1,335,339.

Acylation of the diol is carried out according to known methods such as, e.g., reacting the diol with the corresponding acid anhydride or acid halide under basic conditions. The formation of ester VI appears to take place via an allylic rearrangement of ester III when a basic environment is not provided during acylation.

Ester IV is a dehydration product prepared by acid treatment of ester III at elevated temperature. This ester is also found as a by-product resulting from a partial dehydration which takes place during the preparation of ester VI.

Ester V is formed as a by-product resulting from an allylic rearrangement occurring during the preparation of ester III. It is also found as a product resulting from aqueous acid treatment of ester III at room temperature.

Specific examples of esters of formulae III to VI include, among others, the following:

2,6,6-trimethyl-1-hydroxy-1-(3-acetoxy-but-1-ynyl)cyclohex-2-ene 2,6,6-trimethyl-1-(3-acetoxy-but-1-ynyl)cyclohexa-1,3-diene 2,6,6-trimethyl-1-(3-benzoyloxy-but-1-ynyl)cyclohexa-1,3-diene 2,6,6-trimethyl-1-hydroxy-1-(3-benzoyloxy-but-1-ynyl)-cyclohex-2-ene 2,6,6-trimethyl-3-hydroxy-1-(3-acetoxy-but-1-ynyl)cyclohex-1-ene 2,6,6-trimethyl-3-hydroxy-1-(3-benzoyloxy-but-1-ynyl)-cyclohex-1-ene 2,6,6-trimethyl-3-acetoxy-1-(3-acetoxy-but-1-ynyl)cyclohex-1-ene 2,6,6-trimethyl-3-benzoyloxy-1-(3-benzoyloxy-but-1-ynyl)cyclohex-1-ene 2,6,6-trimethyl-1-hydroxy-1-(3-propionyloxy-but-1-ynyl)cyclohex-2-ene 2,6,6-trimethyl-1-(3-propionyloxy-but-1-ynyl)-cyclohexa-1,3-diene The esters of formulae III, V and VI are produced as mixtures of diastereoisomers from the corresponding diastereoisomeric diols. The isomer mixtures can be used as such in preparing the desired 1-crotonoyl-2,6,6-trimethylcyclohexa-1,3-diene since the product ketone does not exhibit the same diastereoisomerism.

Conversion of the esters of formulae III to VI to 1-crotonoyl-2,6,6-trimethylcyclohexa-1,3-diene takes place smoothly and spontaneously by treating them with a catalytic amount of an essentially anhydrous proton acid. The reaction is carried out in an organic solvent which forms an azeotrope with the water generated by the reaction under temperature and reflux conditions such that the water is continuously removed.

Acids which can be employed in the reaction are either mineral acids such as phosphoric, nitric and sulfuric acid or organic carboxylic acids such as acetic acid, haloacetic acids, propionic acid, or sulfonic acids such as p-toluenesulfonic acid. Acidic agents such as acid cation exchange resins and acidic diatomaceous earth can also be used. Preferred acids are p-toluenesulfonic acid and phosphoric acid.

It is necessary that the acid be essentially anhydrous. In the context of this invention, essentially anhydrous means no more than about 15% by weight water. It is found that in acid of lower concentration, the yield of the desired 1-crotonoyl-2,6,6-trimethylcyclohexa-1,3-diene is adversely affected due to the presence of water.

Relatively small, catalytic amounts of the essentially anhydrous acid are required. About 0.2 to 5 mole % of the acid, based on the acetate, is sufficient to accomplish the dehydration and deacylation.

As suggested hereinabove, the presence of water during the deacylation and dehydration steps is generally undesirable. In order to remove water from the reaction environment, the reaction is carried out in the presence of a solvent which forms an azeotrope with water at a relatively low temperature. Best results are obtained at temperatures between about 40° and 110° C., and preferably between 40° and 70° C. Solvents which form the necessary azeotrope within these temperature limits include, e.g., methylene chloride, chloroform, carbon tetrachloride, benzene, and toluene.

The invention is illustrated by the following examples.

EXAMPLE 1

A.

2,6,6-Trimethyl-1-hydroxy-1-(3-acetoxy-but-1-ynyl)cyclohex-2-ene

In a 250 ml. three-necked flask fitted with a mechanical stirrer, a thermometer and a reflux condenser protected by a calcium chloride tube is stirred a mixture of 42 g. of 2,6,6-trimethyl-1-hydroxy-1-(3-hydroxy-but-1-ynyl)cyclohex-2-ene [prepared in accordance with the method described in Helv. Chim. Acta. 56, 1503 (1973)] and 22 g. of acetic anhydride in 240 ml. of pyridine at ambient temperature for 24 hours. The reaction mixture is then poured into 240 ml. of water and extracted twice with pentane. The combined organic extracts are washed with 10% hydrochloric acid and then with 10% sodium bicarbonate solution and water, dried over sodium sulfate and concentrated to yield a residue which gives on distillation through a short Vigreux column 45 g. (89% yield) of a diastereoisomeric mixture of 2,6,6-trimethyl-1-hydroxy-1-(3-acetoxy-but-1-ynyl)cyclohex-2ene, collected at 188° C./0.6 mm., $n_D^{21}$ 1.4910.

IR (neat): 3490, 3030, 2975, 2920, 2235, 1740, 1454, 1372, 1235, 1171, 1072, 1025, 995, 980, 967, 949, 834, 611 cm$^{-1}$.

NMR (CDCl$_3$): $\delta$1.04 (s, 6H), 1.48 (d, 3H), 1.86 (q, 1H), 2.05 (s, 3H), 2.29 (s, 1H), 5.46 (m, 2H) ppm.

Further distillation affords in ca. 5% yield, 2,6,6-trimethyl-1-hydroxy-1-(3-acetoxybut-1-ynyl)cyclohex-2-ene.

IR (neat): 3420, 2960, 2935, 2865, 2215, 1745, 1450, 1370, 1340, 1233, 1192, 1080, 1040, 1024, 965, 946, 903, 875, 845, 611, 522 cm$^{-1}$.

NMR (CDCl$_3$): $\delta$1.05 (s, 3H), 1.11 (s, 3H), 1.53 (d, 3H), 1.95 (s, 3H), 2.06 (s, 3H), 2.6 (OH), 3.42 (q, 1H), 3.93 (t, 1H), 6.54 (q, 1H) ppm.

B. 1-Crotonoyl-2,6,6-trimethylcyclohexa-1,3-diene

In a 500 ml. three-necked flask fitted with a mechanical stirrer and a Dean-Stark water separator provided with a reflux condenser is placed a solution of 40 g. of 2,6,6-trimethyl-3-hydroxy-1-(3-acetoxy-but-1-ynyl)cyclohex-1-ene in 250 ml. of methylene chloride. The solution is heated to gentle reflux and 1.3 g. of p-toluenesulfonic acid is added. The reaction mixture is refluxed for an additional 5 hours. The mixture is then cooled and poured into 250 ml. of water. The organic layer is separated, washed with 10% sodium bicarbonate solution, then with water and dried over sodium sulfate.

Concentration yields 40 g. of a residue which upon fractionation through a short Vigreux column gives 15 g. (50% yield) of the desired ketone, 1-crotonoyl-2,6,6-trimethylcyclohexa-1,3-diene, b.p. 75°–80° C./0.1 mm., $n^{20}$ 1.5150.

IR (neat): 3040, 2960, 2915, 2890, 2715, 1670, 1645, 1613, 1460, 1441, 1396, 1378, 1357, 1303, 1291, 1250, 1222, 1180, 1156, 1057, 970, 930, 908, 845, 750, 697, 614, 553 cm$^{-1}$.

NMR (CDCl$_3$): $\delta$1.04 (s, 6H), 1.64 (s, 3H), 1.93 (dd, 3H), 5.80 (s, 2H), 6.18 (m, 1H), 6.80 (m, 1H) ppm.

EXAMPLE 2

A.

2,6,6-Trimethyl-1-(3-acetoxy-but-1-ynyl)cyclohexa-1,3-diene

In a 500 ml. three-necked flask fitted with a mechanical stirrer, a dropping funnel, a thermometer and a reflux condenser protected by a calcium chloride tube is placed a mixture of 66 g. of 2,6,6-trimethyl-1-hydroxy-1-(3-hydroxy-but-1-ynyl)cyclohex-2-ene and 76 g. of pyridine in 200 ml. of tertiary butylmethyl ether. To the stirred solution is added 34 g. of acetic anhydride at room temperature. The reaction mixture is stirred for a period of 27 hours at ambient temperature. The reaction mixture is then poured into 200 ml. of water and the organic layer is separated, washed with 10% hydrochloric acid, subsequently with water, 10% sodium bicarbonate solution and water, and finally dried over sodium sulfate. Concentration yields a residue which gives on distillation 33 g. or 45% yield of 2,6,6-trimethyl-1-(3-acetoxy-but-1-ynyl)cyclohexa-1,3-diene, b.p. 125° C./1 mm., $n_D^{20}$ 1.5045.

IR (neat): 3040, 2970, 2940, 2890, 2820, 2210, 1740, 1448, 1370, 1338, 1233, 1080, 1045, 1023, 946, 874, 835, 736, 706, 644, 609 cm$^{-1}$.

NMR (CDCl$_3$): $\delta$1.04 (s, 6H), 1.53 (d, 3H), 1.90 (s, 3H), 2.06 (s, 3H), 5.62 (q, 1H), 5.80 (2H) ppm.

B. 1-Crotonoyl-2,6,6-trimethylcyclohexa-1,3-diene

In a 100 ml. three-necked flask fitted with a mechanical stirrer and a Dean-Stark water separator provided with a reflux condenser, a solution of 5 g. of 2,6,6-trimethyl-1-(3-acetoxy-but-1-ynyl)cyclohexa-1,3-diene in 70 ml. of methylene chloride is refluxed while stirring. Then 0.2 g. of p-toluenesulfonic acid is added and the reaction mixture is refluxed for an additional 4 to 5 hours. The reaction mixture is cooled and poured into 70 ml. of water. The organic layer is separated, subsequently washed with 10% sodium bicarbonate solution and water, and finally dried over sodium sulfate. Concentration yields 5 g. of a residue which gives on distillation 2.5 g. or 60% yield of 1-crotonoyl-2,6,6-trimethylcyclohexa-1,3-diene, b.p. 75°-80° C./0.1 mm., $n_D^{20}$ 1.5150.

EXAMPLE 3

A. 2,6,6-Trimethyl-3-acetoxy-(3-acetoxy-but-1-ynyl)cyclohex-2-ene

In a 100 ml. three-necked flask fitted with a mechanical stirrer and a reflux condenser, a mixture of 10 g. of 2,6,6-trimethyl-1-hydroxy-1-(3-hydroxy-but-1-ynyl)cyclohex-2-ene and 20 g. of acetic anhydride is stirred at reflux temperature for 3 hours. Acetic acid and excess of acetic anhydride are distilled off under vacuo and the residue is distilled through a short Vigreux column. The product is collected as a diastereoisomeric mixture of 2,6,6-trimethyl-3-acetoxy-1-(3-acetoxy-but-1-ynyl)cyclohex-1-ene at 115° C./0.3 mm., $n^{20}$ 1.4910. It contains about 10% of 2,6,6-trimethyl-1-(3-acetoxy-but-1-ynyl)cyclohexa-1,3-diene. The yield is 9 g. or 64%.

IR (neat): 2960, 2935, 2865, 2215, 1740, 1446, 1370, 1340, 1230, 1148, 1080, 1043, 1019, 991, 961, 945, 870, 845, 606 cm$^{-1}$.

NMR (CDCl$_3$): $\delta$1.07 (s, 3H), 1.14 (s, 3H), 1.53 (d, 3H), 1.84 (s, 3H), 2.06 (s, 3H), 2.07 (s, 3H), 5.22 (t, 1H), 5.59 (q, 1H) ppm.

B. 1-Crotonoyl-2,6,6-trimethylcyclohexa-1,3-diene

In a 100 ml. three-necked flask fitted with a mechanical stirrer and a Dean-Stark water separator provided with a reflux condenser, a solution of 7 g. of 2,6,6-trimethyl-3-acetoxy-1-(3-acetoxy-but-1-ynyl)cyclohexlene in 70 ml. of methylene chloride is refluxed while stirring. Then 0.7 g. of p-toluenesulfonic acid is added and the reaction mixture is refluxed for an additional 7 hours. The reaction mixture is cooled and then poured into 70 ml. of water. The organic layer is separated, washed with 10% sodium bicarbonate solution and water. Drying over sodium sulfate and subsequent concentration yields 5 g. of a residue which gives, upon distillation using a short Vigreux column, 3 g. or 60% yield of 1-crotonoyl-2,6,6-trimethylcyclohexa-1,3-diene, b.p. 75°-80° C./0.1 mm, $n_D^{20}$ 1.5150.

EXAMPLE 4

1-Crotonoyl-2,6,6-trimethylcyclohexa-1,3-diene

In a 2 l. three-necked flask fitted with a mechanical stirrer and a Dean-Stark water separator provided with a reflux condenser is placed a solution of 90 g. of crude 2,6,6-trimethyl-1-hydroxy-(3-benzoyloxy-but-1-ynyl)-cyclohex-2ene [isolated from benzoylation of the corresponding diol, for the synthesis of the diol, see Helv. Chim. Acta 56, 1503 (1973) and ibid. 56, 1514 (1973)] in 600 ml. of alcohol free chloroform. Then 3 g. of p-toluenesulfonic acid is added and the reaction mixture is heated to reflux while stirring. Reflux is continued for 2 hours, while water is separated off. The reaction mixture is cooled and then poured into 600 ml. of water. The organic layer is separated, washed three times with 10% sodium bicarbonate solution to remove benzoic acid and then with water until neutral. Drying over sodium sulfate and subsequent concentration yields a residue which is flash-distilled. Redistillation using a short Vigreux column gives 22 g. or 40% yield of 1-crotonoyl-2,6,6-trimethylcyclohexa-1,3-diene, b.p. 75°-80° C./0.1 mm., $n_D^{20}$ 1.5170.

What I claimed and desired to protect by Letters Patent is:

1. A method of preparing 1-crotonoyl-2,6,6-trimethylcyclohexa-1,3-diene which comprises treating a compound having the general formula

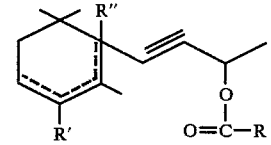

where R is a 1 to 6 carbon alkyl group, a phenyl radical or an alkylphenyl radical, the dotted lines represent a sole double bond in the 1- or 2-position or conjugated double bonds in the 1,3-position, and when the double bond is in the 1-position only, R' is hydroxyl or

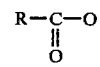

and R'' is absent, when the double bond is in the 2-position, R'' is hydroxyl and R' is absent, and when conjugated double bonds are present, R' is hydrogen and R'' is absent with a catalytic amount of an essentially anhydrous mineral or organic proton acid reagent in an organic solvent capable of forming an azeotrope with water.

2. The method of claim 1 wherein the proton acid reagent is phosphoric acid, p-toluenesulfonic acid, acidic diatamaceous earth, or an acid cation exchange resin.

3. The method of claim 2 wherein the starting material has the formula

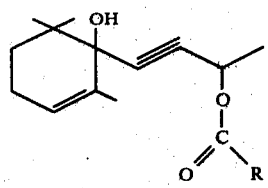

4. The method of claim 3 wherein the starting material is 2,6,6-trimethyl-1-hydroxy-1-(3-acetoxy-but-1-ynyl)cyclohex-2ene and the proton acid reagent is p-toluenesulfonic acid.

5. The method of claim 3 wherein the starting material is 2,6,6-trimethyl-1-hydroxy-1-(3-benzoyloxy-but-1-ynyl)cyclohex-2-ene and the proton acid reagent is p-toluenesulfonic acid.

6. A chemical compound having the general structural formula

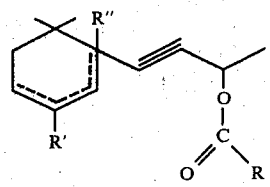

wherein R is a 1 to 6 carbon alkyl group, a phenyl radical or an alkylphenyl radical, the dotted lines represent a sole double bond in the 1- or 2-position or conjugated double bonds in the 1,3-position, and when the double bond is in the 1-position only, R' is hydroxyl or

and R" is absent, when the double bond is in the 2-position, R" is hydroxyl and R' is absent, and when conjugated double bonds are present, R' is hydrogen and R" is absent.

7. 2,6,6-Trimethyl-1-hydroxy-1-(3-acetoxy-but-1-ynyl)cyclohex-2-ene.

8. 2,6,6-Trimethyl-1-hydroxy-1-(3-benzoyloxy-but-1-ynyl)cyclohex-2-ene.

9. 2,6,6-Trimethyl-3-acetoxy-1-(3-acetoxy-but-1-ynyl)cyclohex-1-ene.

10. 2,6,6-Trimethyl-3-benzoyloxy-1-(3-benzoyloxy-but-1-ynyl)cyclohex-1-ene.

* * * * *